United States Patent
Chah et al.

(10) Patent No.: US 10,398,776 B1
(45) Date of Patent: Sep. 3, 2019

(54) PHONOPHORETIC CANNABIDIOL COMPOSITION AND TRANSDERMAL DELIVERY SYSTEM

(71) Applicant: Essential Green Goodness LLC, Mount Dora, FL (US)

(72) Inventors: Shamaya Chah, Apopka, FL (US); Nicholas Bart Magrone, Sr., Mount Dora, FL (US)

(73) Assignee: Essential Green Goodness LLC, Mount Dora, FL (US)

( * ) Notice: Subject to any disclaimer, the term of this patent is extended or adjusted under 35 U.S.C. 154(b) by 853 days.

(21) Appl. No.: 14/930,979

(22) Filed: Nov. 3, 2015

Related U.S. Application Data (60) Provisional application No. 62/122,939, filed on Nov. 3, 2014.

(51) Int. Cl.
  *A61K 41/00* (2006.01)
  *A61K 31/05* (2006.01)
  *A61N 7/00* (2006.01)

(52) U.S. Cl.
  CPC .......... *A61K 41/0047* (2013.01); *A61K 31/05* (2013.01); *A61N 7/00* (2013.01)

(58) Field of Classification Search
  None
  See application file for complete search history.

(56) References Cited

U.S. PATENT DOCUMENTS

| | | | | |
|---|---|---|---|---|
| 2010/0273895 | A1* | 10/2010 | Stinchcomb | A61K 9/0014 514/733 |
| 2012/0207827 | A1* | 8/2012 | Cozean | A61K 9/0014 424/463 |

OTHER PUBLICATIONS

Motallebnejad, et al., The Journal of Contemporary Dental Practice, 9:1. (Year: 2008).*
Reynolds, et al., Journal of Ethnopharmacology, 68:3. (Year: 1999).*
Cohen, et al, Therapeutics, 8:154. (Year: 2003).*

* cited by examiner

*Primary Examiner* — Michael Barker
(74) *Attorney, Agent, or Firm* — Malloy & Malloy, PL (57) ABSTRACT

A phonophoretic cannabidiol composition comprises an amount of cannabidiol, an amount of a glucose source, such as honey, an amount of aloe vera, and amounts of one or more of glucosamine, methylsulfonylmethane, and chondroitin. A transdermal delivery system for administration of a phonophoretic cannabidiol composition includes a phonophoretic cannabidiol composition, a laser generator comprising an emitter which generates and directs a laser beam to the treatment area, and an ultrasound generator comprising a transducer which generates and transmits a plurality of ultrasonic waves to the treatment area. A method for transdermal delivery of a phonophoretic cannabidiol composition includes selecting laser pretreatment parameters, directing a laser beam to the treatment area, applying an amount of a phonophoretic cannabidiol composition to a treatment area, selecting ultrasonic treatment parameters, and, transmitting a plurality of ultrasonic waves to the treatment area.

13 Claims, 4 Drawing Sheets

PHONOPHORETIC CANNABIDIOL COMPOSITION AND TRANSDERMAL DELIVERY SYSTEM

BACKGROUND OF THE INVENTION

Field of the Invention

The present invention is directed to a cannabidiol composition specifically formulated for transdermal delivery to an affected area of a patient via phonophoresis. In at least one embodiment, the novel composition comprises amounts of cannabidiol, a glucose source, aloe vera, glucosamine, methylsulfonylmethane, and chondroitin. A system for transdermal delivery of the novel phonophoretic cannabidiol composition comprises a laser generator and an ultrasound generator, and the present invention further comprises a method for implementing transdermal delivery via the present system.

Description of the Related Art

Transdermal delivery of a variety of beneficial compounds is well known. Among the more common applications are the nicotine containing "patches" which are intended to aid person's trying to quit smoking cigarettes. Typically, transdermal delivery of a desired compound occurs via migration of the compound across the dermal boundaries of a patient's skin into his or bloodstream by further migration into the small blood vessels which are present close to the surface of a person's skin.

While known transdermal delivery systems are effective for the administration of many beneficial compounds to a patient, as will be appreciated, transdermal delivery into the blood stream of a patient is ineffective for the treatment of affected areas of a patient's body which receive little or no blood flow. One such example is cartilage. Cartilage is made up of specialized cells called chondrocytes which produce large amounts of extracellular matrix composed of collagen fibers, proteoglycan, and elastin fibers. There are no blood vessels in cartilage to supply the chondrocytes with nutrients, rather, nutrients diffuse through connective tissue surrounding the cartilage, called the perichondrium, and into the core of the cartilage. Due to the lack of blood vessels, cartilage grows and repairs more slowly than other tissues.

As such, it would be beneficial to provide a composition which is specifically formulated for transdermal delivery to an affected area of patient which receives little to no blood flow. More in particular, it would be beneficial to provide a cannabidiol composition which may be administered transdermally into the cartilage of patient via phonophoresis. A further benefit may be realized by providing a system and method of transdermal delivery of a phonophoretic composition directly into the cartilage of patient.

SUMMARY OF THE INVENTION

Cannabidiol compounds are known to impart beneficial therapeutic effects on various areas of the human physiology. Among the tissues which may benefit from treatment with cannabidiol compounds is damaged cartilage. As noted above, since cartilage contain no blood vessels, delivery of beneficial compounds to the cartilage of a patient via standard transdermal mechanisms is ineffective.

As such, the present invention comprises a cannabidiol composition specifically formulated for transdermal delivery into cartilage via phonophoresis.

In accordance with one embodiment of the present invention, a phonophoretic cannabidiol composition comprises an amount of cannabidiol, an amount of the glucose source, and an amount of aloe vera. A phonophoretic cannabidiol composition in accordance with one further embodiment of the present invention comprises an amount of cannabidiol in the range of about 1 to 5 percent by weight, an amount of a glucose source in a range of about 10 to 20 percent by weight, and an amount of aloe vera in a range of about 40 to 60 percent by weight. In one further embodiment of a phonophoretic cannabidiol composition in accordance with the present invention comprises one or more of glucosamine, methylsulfonylmethane, and chondroitin in amounts in a range of about 5 to 15 percent by weight each.

In at least one embodiment, a phonophoretic cannabidiol composition in accordance with the present invention comprises an amount of cannabidiol of about 2 percent by weight, an amount of a glucose source, such as honey, of about 14 percent by weight, an amount of aloe vera of about 54 percent by weight, an amount of glucosamine of about 10 percent by weight, an amount of methylsulfonylmethane of about 10 percent by weight, and an amount of chondroitin of about 10 percent by weight.

The present invention further comprises a transdermal delivery system for administration of a phonophoretic cannabidiol composition. In at least one embodiment, a transdermal delivery system comprises a phonophoretic composition including an amount of cannabidiol, an amount of a glucose source, and an amount of aloe vera. In at least one further embodiment, a transdermal delivery system comprises a phonophoretic composition including cannabidiol, a glucose source, aloe vera, glucosamine, methylsulfonylmethane, and chondroitin. In accordance with at least one embodiment of the present invention, a transdermal delivery system comprises a laser generator comprising an emitter which generates and directs a laser beam having a wavelength in a far infrared region to the treatment area of the patient. One further embodiment of a transdermal delivery system in accordance with the present invention also comprises an ultrasound generator comprising a transducer which generates and transmits a plurality of ultrasonic waves having a frequency in an ultrasonic range to the treatment area of the patient.

As stated above, the present invention also comprises a method for transdermal delivery of a phonophoretic cannabidiol composition. In at least one embodiment, the method includes selecting laser pretreatment parameters, directing a far infrared laser beam to the treatment area for a predetermined pretreatment period, applying an amount of a phonophoretic cannabidiol composition to the treatment area of the patient, selecting ultrasonic treatment parameters, and, transmitting a plurality of ultrasonic waves to the treatment area of the patient for a predetermined treatment period.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION

Figure 1:
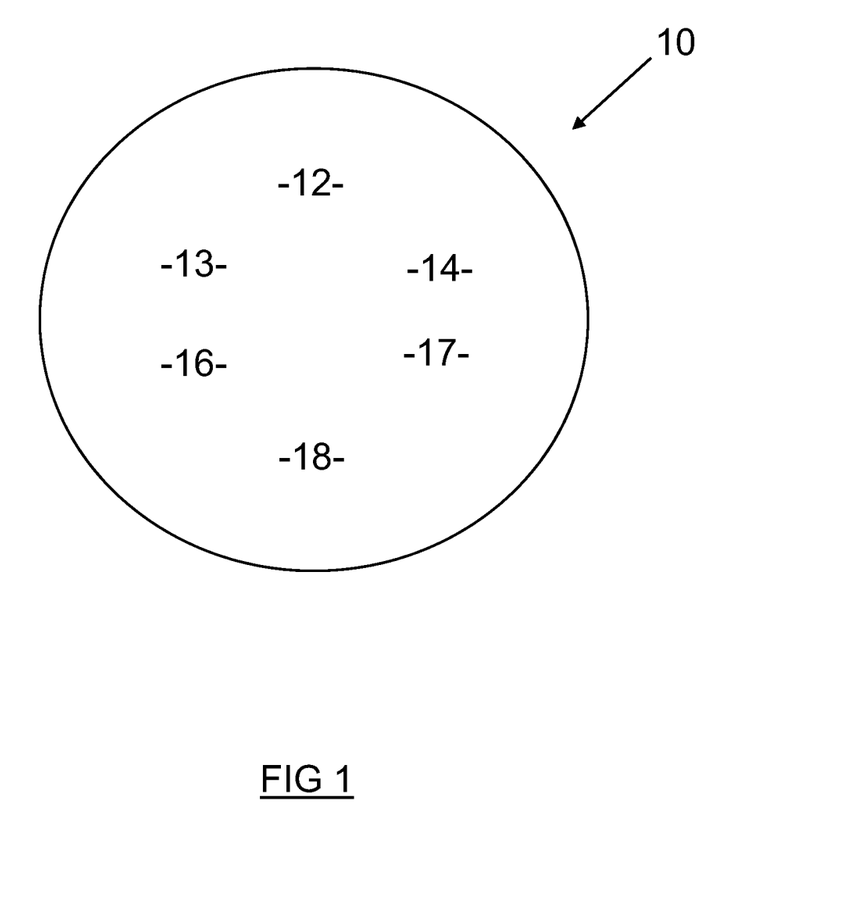
FIG. 1 is a diagrammatic representation of one illustrative embodiment of a phonophoretic cannabidiol composition in accordance with the present invention.

As stated above, the present invention is directed to a phonophoretic cannabidiol composition 10, such as is diagrammatically represented in the illustrative embodiment of FIG. 1. A phonophoretic cannabidiol composition 10 in accordance with the present invention includes at least an amount of cannabidiol 12. In at least one embodiment, cannabidiol 12 is obtained from industrial hemp plants, which do not present regulatory restraints on cultivation due to the relatively low amounts of the psychoactive component tetrahydrocannabinol, which is found in other strains of plants of the genus *cannabis*. Looking further to FIG. 1, a phonophoretic cannabidiol composition 10 in accordance with at least one embodiment of the present invention also comprises an amount of a glucose source 13. As will be appreciated by those of skill in the art, a glucose source is required by living cells, and incorporation of a glucose source 13 into the present phonophoretic cannabidiol composition 10 induces living cells to allow the present phonophoretic cannabidiol composition 10 to migrate across cell walls.

Further, and as also disclosed above, in at least one embodiment a phonophoretic cannabidiol composition 10 comprises an amount of aloe vera 14. Aloe vera 14 is incorporated into the present phonophoretic cannabidiol composition 10 in order to improve permeability of the composition 10 through the skin and the underlying subcutaneous tissue. Furthermore, the present of plant matter will maximize the bioavailability of the composition 10.

In at least one embodiment, a phonophoretic cannabidiol composition 10 in accordance with the present invention includes an amount of one or more of glucosamine 16, methylsulfonylmethane 17, and chondroitin 18. In yet one further embodiment, a phonophoretic cannabidiol composition 10 in accordance with the present invention includes an amount of each of glucosamine 16, methylsulfonylmethane 17, and chondroitin 18. Both glucosamine 16 and chondroitin 18 are components of cartilage, and are incorporated into a phonophoretic cannabidiol composition 10 in accordance with the present invention to facilitate regeneration and elasticity of affected cartilage being treated. Methylsulfonylmethane 17 is an anti-inflammatory and as such methylsulfonylmethane 17 is incorporated in at least one embodiment of a phonophoretic cannabidiol composition 10 in accordance with the present invention to help minimize inflammation in a treatment area of a patient, as well as to provide usable sulfur thereto.

In accordance with at least one embodiment of the present invention, a phonophoretic cannabidiol composition 10 comprises an amount of cannabidiol 12 in a range of about 1 to 5 percent by weight. In one further embodiment, a phonophoretic cannabidiol composition 10 includes an amount of cannabidiol 12 of about 2 percent by weight.

A phonophoretic cannabidiol composition 10 in accordance with one embodiment of the present invention comprises an amount of a glucose source 13 in a range of about 10 to 20 percent by weight. In at least one embodiment, a phonophoretic cannabidiol composition 10 comprises an amount of a glucose source 13 of about 14 percent by weight. In one embodiment, a glucose source 13 in accordance with the present invention comprises honey. In yet one further embodiment, a glucose source 13 in accordance with the present invention comprises organic honey.

With regard to aloe vera 14, a phonophoretic cannabidiol composition 10 in accordance with at least one embodiment of the present invention comprises an amount of aloe vera 14 in a range of about 40 to 60 percent by weight. In one further embodiment, a phonophoretic cannabidiol composition 10 comprises an amount of aloe vera 16 of about 54 percent by weight.

One or more of glucosamine 16, methylsulfonylmethane 17, and chondroitin 18 are present in an amount of about 5 to 15 percent by weight each in at least one embodiment of a phonophoretic cannabidiol composition 10 in accordance with the present invention. In yet one further embodiment, each of glucosamine 16, methylsulfonylmethane 17, and chondroitin 18 are present in amounts of about 5 to 15 percent by weight each in a phonophoretic cannabidiol composition 10 in accordance with the present invention. In at least one embodiment, a phonophoretic cannabidiol composition 10 in accordance with the present invention comprises an amount of glucosamine 16 of about 10 percent by weight, an amount of methylsulfonylmethane 17 of about 10 percent by weight, and an amount of chondroitin 18 of about 10 percent by weight.

In view of the foregoing, it follows that in at least one embodiment, a phonophoretic cannabidiol composition 10 in accordance with the present invention comprises an amount of cannabidiol 12 of about 2 percent by weight, an amount of a glucose source 13, such as honey or organic honey, of about 14 percent by weight, an amount of aloe vera 14 of about 54 percent by weight, an amount of glucosamine 16 of about 10 percent by weight, an amount of methylsulfonylmethane 17 of about 10 percent by weight, and an amount of chondroitin 18 of about 10 percent by weight.

Figure 2:
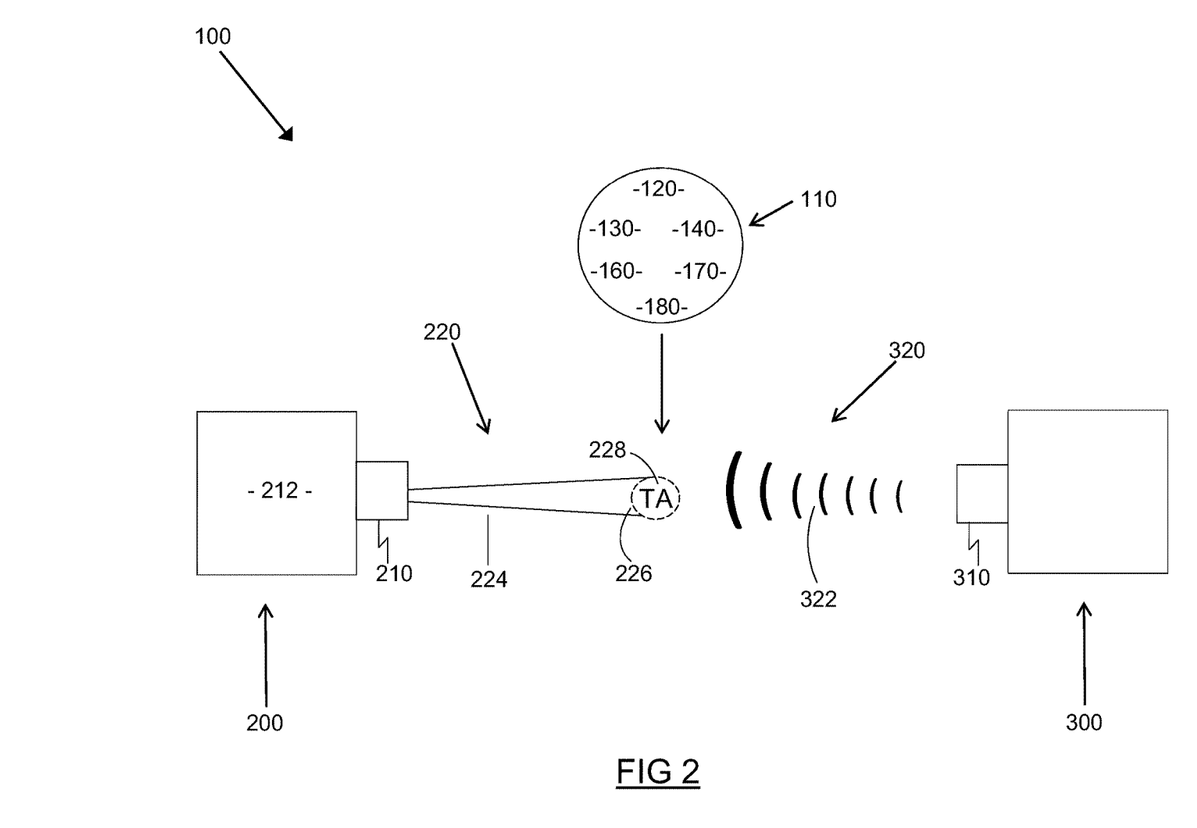
FIG. 2 is a schematic representation of one illustrative embodiment of a system for transdermal delivery of a phonophoretic cannabidiol composition to an affected area of a patient in accordance with the present invention.

As also disclosed above, the present invention comprises a transdermal delivery system 100 for a phonophoretic cannabidiol composition, as shown in the illustrative embodiment of FIG. 2. With reference to FIG. 2, the present transdermal delivery system 100 comprises an amount of a phonophoretic cannabidiol composition 110. As before, a phonophoretic cannabidiol composition 110 in accordance with at least one embodiment of the present invention comprises an amount of cannabidiol 120, an amount of a glucose source 130, and an amount of aloe vera 140. Also as before, a phonophoretic cannabidiol composition in accordance with the present invention comprises an amount of cannabidiol 120 in a range of about 1 to 5 percent by weight, an amount of a glucose source 130 in a range of about 10 to 20 percent by weight, an amount of aloe vera 140 in a range of about 40 to 60 percent by weight, and one or more of glucosamine 160, methylsulfonylmethane 170, and chondroitin 180 in an amount of about 5 to 15 percent by weight.

In at least one further embodiment, a phonophoretic cannabidiol composition 110 in accordance with the present transdermal delivery system 100 comprises an amount of cannabidiol 120 of about 2 percent by weight, an amount of a glucose source 130, such as honey or organic honey, of about 14 percent by weight, an amount of aloe vera 140 of about 54 percent by weight, an amount of glucosamine 160 of about 10 percent by weight, an amount of methylsulfonylmethane 170 of about 10 percent by weight, and an amount of chondroitin 180 of about 10 percent by weight.

With further reference to the illustrative embodiment of FIG. 2, a transdermal delivery system 100 for a phonophoretic cannabidiol composition comprises a laser generator, generally as shown as at 200. As shown in the illustrative embodiment of FIG. 2, the laser generator 200 comprises an emitter 210 which generates a laser beam 220, such as may be directed towards a treatment area ("TA") of a patient. A laser generator 200 in accordance with the present invention has a defined power output 212 which, in at least one embodiment is in a range of about 2,000 miliwatts. In at least one embodiment, a laser generator 200 in accordance with the present invention comprises a gallium-aluminum-arsenide ("GaAlAs") infrared laser as a light source. In one further embodiment, a laser generator 200 in accordance with the present invention, generates a laser beam 220 having a wavelength 222 in a range of about 810 nanometers. As will be appreciated by those with skill in the art, a laser beam having a wavelength in a range of about 810 nanometers at least partially defines a laser beam in the far infrared region of the visible light spectrum.

In accordance with one embodiment of the present invention, a laser generator 200 comprises a class 3B laser. More in particular, in one embodiment, a laser generator 200 comprises a plurality of emitters 210, and in at least one embodiment, a laser generator 200 comprises four emitters 210. Additional operating parameters of a laser generator 200 in accordance with at least one embodiment of the present invention include a total power output 212 in a range of about 2,000 milliwatts, an aperture of 9.5 and a beam divergence of 9*×38*. In one further embodiment, the polarization of the laser beam 220 is linear.

In one embodiment, a laser generator 200 in accordance with the present invention is positioned such that the laser beam 220 presents a spot size in a range of about 0.5 to 1.0 square centimeters at the treatment area of the patient. In at least one further embodiment, a laser generator 200 is positioned relative to the patient such that a laser beam 220 presents a spot size of about 0.7 square centimeters at the treatment area of the patient. In one further embodiment, a laser generator 200 generates a laser beam 220 which produces a power density 228 of about 0.5 to 1.0 watts per square centimeter at the treatment area of the patient. In at least one embodiment, a power density 228 is about 0.8 watts per square centimeter at the treatment area of the patient. As will be appreciated by those with skill in the art a laser beam having a spot size of about 0.7 square centimeters and a power density 228 of about 0.8 watts per square centimeter is capable of generating an energy flux of at least about 50 joules per square centimeter at the treatment area of the patient.

Looking once again to the illustrative embodiment of FIG. 2, the transdermal delivery system 100 for a phonophoretic cannabidiol composition in accordance with the present invention further comprises an ultrasound generator 300. In at least one embodiment, the ultrasound generator 300 comprises a transducer 310 which generates a plurality of ultrasonic waves 320, such as is shown in FIG. 2. As will be appreciated by those with skill in the art an ultrasonic wave 320 is defined by a number of parameters, including at least a wave frequency 322. In at least one embodiment, an ultrasound generator 300 generates a plurality of ultrasonic waves 320 having a frequency in a range of about 1 to 3 megahertz.

Figure 3:
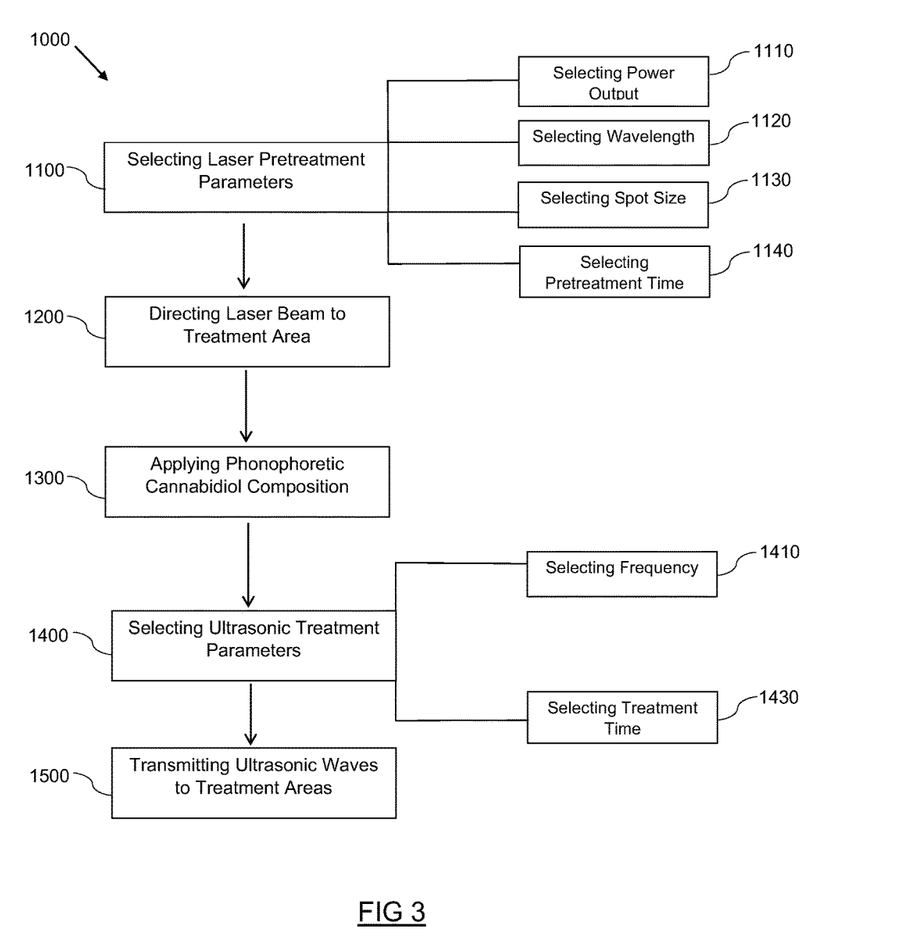
FIG. 3 is a diagrammatic representation of one illustrative embodiment of a method for implementing transdermal delivery of a phonophoretic cannabidiol composition to a patient in accordance with the present invention.

Turning next to the illustrative embodiment of FIG. 3, the present invention further comprises a method for transdermal delivery of a phonophoretic cannabidiol composition 1000 to a treatment area of a patient.

As shown in the illustrative embodiment of FIG. 3, the present method 1000 comprises selecting laser pretreatment parameters 1100. In at least one embodiment, selecting a plurality of laser pretreatment parameters 1100 includes, by way of example only, selecting a power output 1110 of a laser generator, selecting a wavelength 1120 for a laser beam, selecting a spot size 1130 presented by a laser beam at a treatment area of a patient, and/or selecting a pretreatment time 1140 for exposure of a treatment area of a patient to a laser beam.

In at least one embodiment, the present method 1000 comprises selecting a power output 1110 in a range of about 2,000 milliwatts. In one further embodiment, the present method 1000 comprises selecting a wavelength 1120 of a laser beam in the far infrared range of the visible spectrum. In still one further embodiment, the present method comprising selecting a spot size 1130 a laser beam presents at a treatment area of a patient in a range of about 0.5 to 1.0 square centimeters, and in one further embodiment, selecting a spot size 1130 of about 0.7 square centimeters.

The method 1000 in accordance with at least one embodiment of the present invention further comprises directing an infrared laser beam to a treatment area of a patient 1200 for a preselected pretreatment time. In at least one embodiment, the present method comprises selecting a pretreatment time 1140 in a range of about one to five minutes. In at least one further embodiment, the present method comprises selecting a pretreatment time 1140 of about two minutes.

As will be appreciated by those of skill in the art, directing a laser beam to a treatment area of a patient 1300 will improve the receptiveness of the cells in the treatment area to the migration of a transdermal composition therethrough. In at least one embodiment, a laser beam is directed to a treatment area of a patient 1300 for a predetermined treatment time 1140 of between about one to two minutes, as before. In one further embodiment, a laser beam is directed to a portion of a treatment area of a patient 1300 in a static application for between about 5 to 30 seconds before the laser is redirected to another portion of the treatment area, for a total pretreatment time of about one to two minutes.

The method 1000 in accordance with at least one embodiment of the present invention further comprises applying an amount of a phonophoretic cannabidiol composition 1300 to a treatment area of a patient. In at least one embodiment, a phonophoretic composition includes an amount of cannabidiol, an amount of a glucose source, an amount of aloe vera, an amount of glucosamine, an amount of methylsulfonylmethane, and an amount of chondroitin. In one further embodiment, a phonophoretic cannabidiol composition comprises about 2 percent by weight of cannabidiol, about 14 percent by weight of organic honey, about 54 percent by weight of aloe vera, about 10 percent by weight of glucosamine, about 10 percent by weight of methylsulfonylmethane, and about 10 percent by weight of chondroitin. The amount of phonophoretic compound applied to a treatment area of a patient 1300 in accordance with at least one embodiment of the present invention is about one gram.

Looking once again to the illustrative embodiment of FIG. 3, a method of transdermal delivery of a phonophoretic cannabidiol composition 1000 in accordance with at least one embodiment of the present invention further comprises selecting ultrasonic treatment parameters 1400. As before, in at least one embodiment, the present method 1000 comprises selecting a plurality of ultrasonic treatment parameters 1400, such as, by way of example, selecting a frequency 1410 of a plurality of ultrasonic waves. In at least one embodiment, the present method 1000 comprises selecting a frequency 1410 in a range of about one to three megahertz. In one further embodiment, the present method 1000 comprises selecting a treatment time 1430 for exposure of a treatment area of a patient to a plurality of ultrasonic waves.

The method 1000 in accordance with at least one embodiment of the present invention further comprises directing a plurality of ultrasonic waves to a treatment area of a patient 1500 for a preselected treatment time. In at least one embodiment, the present method comprises selecting a treatment time 1430 in a range of about five to forty minutes. In at least one further embodiment, the present method comprises selecting a treatment time 1430 of about ten to twenty minutes.

As will be appreciated by those of skill in the art, transmitting a plurality of ultrasonic waves to a treatment area of a patient 1500 will drive a phonophoretic composition through the dermal layer and into a targeted tissue of the patient, such as, a section of cartilage.

Figure 4:
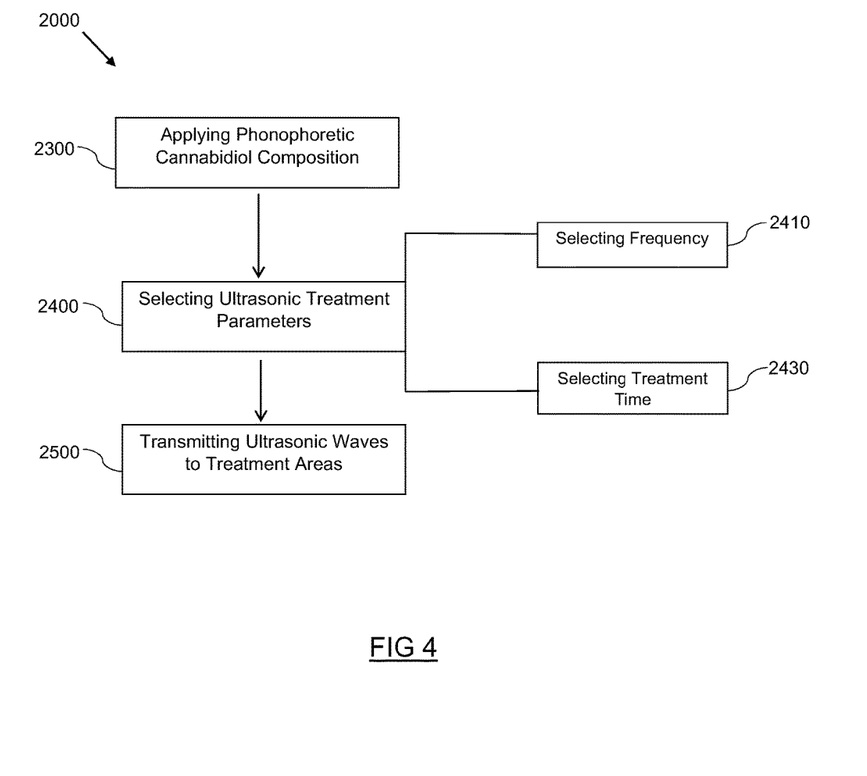
FIG. 4 is a diagrammatic representation illustrative of one alternative embodiment of a method for implementing transdermal delivery of a phonophoretic cannabidiol composition to a patient in accordance with the present invention.

FIG. 4 is a diagrammatic representation illustrative of one alternative embodiment of a method for transdermal delivery of a phonophoretic cannabidiol composition 2000 to a treatment area of a patient. Notably, and unlike the method presented in accordance with the illustrative embodiment of FIG. 3, the method 2000 in accordance with FIG. 4 does not include laser pretreatment and associated steps.

To begin, the method 2000 in accordance with at the alternative embodiment of FIG. 4 comprises applying an amount of a phonophoretic cannabidiol composition 2300 to a treatment area of a patient. In at least one embodiment, a phonophoretic composition includes an amount of cannabidiol, an amount of a glucose source, an amount of aloe vera, an amount of glucosamine, an amount of methylsulfonylmethane, and an amount of chondroitin. As before, in one further embodiment, a phonophoretic cannabidiol composition comprises about 2 percent by weight of cannabidiol, about 14 percent by weight of organic honey, about 54 percent by weight of aloe vera, about 10 percent by weight of glucosamine, about 10 percent by weight of methylsulfonylmethane, and about 10 percent by weight of chondroitin. The amount of phonophoretic compound applied to a treatment area of a patient 2300 in accordance with alternative embodiment of FIG. 4 is about one gram.

Looking further to the illustrative embodiment of FIG. 4, the method of transdermal delivery of a phonophoretic cannabidiol composition 2000 further comprises selecting ultrasonic treatment parameters 2400. As before, in at least one embodiment, selecting a plurality of ultrasonic treatment parameters 2400 includes, by way of example, selecting a frequency 2410 of a plurality of ultrasonic waves. In at least one embodiment, the present method 2000 comprises selecting a frequency 2410 in a range of about one to three megahertz. In one further embodiment, the present method 2000 comprises selecting a treatment time 2430 for exposure of a treatment area of a patient to a plurality of ultrasonic waves.

The method 2000 in accordance with at least one embodiment of the present invention further comprises directing a plurality of ultrasonic waves to a treatment area of a patient 2500 for a preselected treatment time. In at least one embodiment, the present method comprises selecting a treatment time 2430 in a range of about five to forty minutes. In at least one further embodiment, the present method comprises selecting a treatment time 1430 of about ten to twenty minutes.

As will be appreciated by those of skill in the art, transmitting a plurality of ultrasonic waves to a treatment area of a patient 2500 will drive a phonophoretic composition through the dermal layer and into a targeted tissue of the patient, such as, a section of cartilage.

Since many modifications, variations and changes in detail can be made to the described embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A phonophoretic cannabidiol composition formulated for application to a patient's skin and transdermal delivery to a portion of the patient's cartilage in a treatment area, said composition comprising:
   an amount of cannabidiol,
   an amount of a glucose source to induce living cells to allow said composition to migrate across the cells and for metabolization therein,
   an amount of aloe vera to improve permeability of said composition through the patient's skin and underlying subcutaneous tissue, and
   an amount of one or more of glucosamine and chondroitin to facilitate regeneration and elasticity of the portion of the patient's cartilage, and methylsulfonylmethane to reduce inflammation in the treatment area and to provide usable sulfur thereto.

2. The composition as recited in claim 1 wherein said amount of cannabidiol is about 1 to 5 percent by weight.

3. The composition as recited in claim 1 wherein said amount of said glucose source is about 10 to 20 percent by weight.

4. The composition as recited in claim 3 wherein said glucose source comprises organic honey.

5. The composition as recited in claim 1 wherein said amount of aloe vera is about 40 to 60 percent by weight.

6. The composition as recited in claim 1 wherein said amount of glucosamine is about 5 to 15 percent by weight.

7. The composition as recited in claim 1 wherein said amount of methylsulfonylmethane is about 5 to 15 percent by weight.

8. The composition as recited in claim 1 wherein said amount of chondroitin is about 5 to 15 percent by weight.

9. The composition as recited in claim 1 wherein said amount of cannabidiol is about 2 percent by weight, said amount of said glucose source is about 14 percent by weight, said amount of aloe vera is about 54 percent by weight, said amount of glucosamine is about 10 percent by weight, said amount of methylsulfonylmethane is about 10 percent by weight, and said amount of chondroitin is about 10 percent by weight.

10. A method for transdermal delivery of the phonophoretic cannabidiol composition of claim 1 through a treatment area directly into a section of cartilage of a patient, said method comprising:
   selecting laser pretreatment parameters,
   directing a far infrared laser beam to the treatment area for a predetermined pretreatment period,
   applying an amount of a phonophoretic cannabidiol composition to the treatment area of the patent, selecting ultrasonic treatment parameters, and transmitting a plurality of ultrasonic waves to the treatment area of the patent for a predetermined treatment period.

11. The method as recited in claim 10 wherein the phonophoretic cannabidiol composition comprises about 2 percent by weight of cannabidiol, about 14 percent by weight of organic honey, about 54 percent by weight of aloe vera, about 10 percent by weight of glucosamine, about 10 percent by weight of methylsulfonylmethane, and about 10 percent by weight of chondroitin.

12. The method as recited in claim 10 wherein the predetermined pretreatment period for directing a far infrared laser beam to the treatment area of the patient is about two minutes.

13. The method as recited in claim 10 wherein the predetermined treatment period for transmitting a plurality of ultrasonic waves to the treatment area of the patent is about ten to twenty minutes.

\* \* \* \* \*

UNITED STATES PATENT AND TRADEMARK OFFICE
CERTIFICATE OF CORRECTION

| | | |
|---|---|---|
| PATENT NO. | : 10,398,776 B1 | Page 1 of 1 |
| APPLICATION NO. | : 14/930979 | |
| DATED | : September 3, 2019 | |
| INVENTOR(S) | : Chah | |

It is certified that error appears in the above-identified patent and that said Letters Patent is hereby corrected as shown below:

On the Title Page

Item (12) delete "Chah, et al." and insert -- Chah --.

Item (72) Inventors:
Should read:
-- (72) Inventor: Shamaya Chah, Miami Beach, (FL) --.

Signed and Sealed this
Twenty-third Day of June, 2020

Andrei Iancu
*Director of the United States Patent and Trademark Office*